United States Patent
Phillips

(10) Patent No.: US 10,208,005 B2
(45) Date of Patent: Feb. 19, 2019

(54) PROCESS FOR MANUFACTURING ETHYLENE OXIDE USING SCALED SELECTIVITY VALUES

(71) Applicant: Dow Technology Investments LLC, Midland, MI (US)

(72) Inventor: Ailene Gardner Phillips, South Charleston, WV (US)

(73) Assignee: Dow Technology Investments LLC, Midland, MI (US)

( * ) Notice: Subject to any disclaimer, the term of this patent is extended or adjusted under 35 U.S.C. 154(b) by 0 days.

(21) Appl. No.: 15/540,076

(22) PCT Filed: Sep. 30, 2015

(86) PCT No.: PCT/US2015/053157
§ 371 (c)(1),
(2) Date: Jun. 27, 2017

(87) PCT Pub. No.: WO2016/108975
PCT Pub. Date: Jul. 7, 2016

(65) Prior Publication Data
US 2017/0362193 A1     Dec. 21, 2017

Related U.S. Application Data

(60) Provisional application No. 62/097,841, filed on Dec. 30, 2014.

(51) Int. Cl.
*C07D 301/10*     (2006.01)
*B01J 23/68*      (2006.01)

(52) U.S. Cl.
CPC .......... *C07D 301/10* (2013.01); *B01J 23/688* (2013.01); *Y02P 20/52* (2015.11)

(58) Field of Classification Search
CPC ....... C07D 301/10; B01J 23/688; Y02P 20/52
(Continued)

(56) References Cited

U.S. PATENT DOCUMENTS

| 9,026,668 B2 | 5/2015 | Harrison |
| 9,386,356 B2 | 7/2016 | Harrison |
| 2010/0267974 A1 | 10/2010 | Zhang et al. |

FOREIGN PATENT DOCUMENTS

| CA | 2972690 A1 | 7/2016 |
| CN | 107406398 A | 11/2017 |

(Continued)

OTHER PUBLICATIONS

International Search Report dated Dec. 18, 2015 for PCT/US2015/053157.

(Continued)

*Primary Examiner* — Taylor V Oh
(74) *Attorney, Agent, or Firm* — Hansen IP Law PLLC

(57) ABSTRACT

Disclosed herein are methods of using scaled selectivities to assist in determining whether changes to the value of a target ethylene oxide production parameter—such as ethylene oxide production rate—used in the process of epoxidizing ethylene with a high-selectivity catalyst, have caused the process to move away from optimal operation. If the deviation from optimal operation has not worsened, it is generally unnecessary to perform a full optimization study even if the value of a target ethylene oxide production parameter has changed, which reduces or eliminates process disturbances caused by carrying out such studies. Methods are also disclosed which use both scaled selectivities and scaled reaction temperatures. If scaled selectivities reveal that a change in the value of a target ethylene oxide production parameter has moved the process away from optimal operation, scaled reaction temperatures can, under certain conditions, provide an indication of the directions in which the (Continued)

reaction temperature and/or overall catalyst chloriding effectiveness should be changed to move toward optimal operation. If a change in the value of a target ethylene oxide production parameter has improved the scaled selectivity, the scaled reaction temperature may also be used to guide further adjustments which may further improve scaled selectivity.

15 Claims, 4 Drawing Sheets

(58) Field of Classification Search
USPC .......................................................... 549/534
See application file for complete search history.

(56) References Cited

FOREIGN PATENT DOCUMENTS

| | | |
|---|---|---|
| EP | 3240781 A1 | 11/2017 |
| KR | 20170100632 A | 9/2017 |
| SG | 11201705409W A | 7/2017 |
| TW | 201629028 A | 8/2016 |
| WO | 2010123844 A1 | 10/2010 |

OTHER PUBLICATIONS

Written Opinion dated Dec. 18, 2015 for PCT/US2015/053157.
Lars C. Grabbow, et al., Descriptor-Based Analysis Applied to HCN Synthesis from NH3 and CH4, Angewandte Chemie International Edition, Wiley—V C H Verlag Gmbh & Co. KGAA, DE, vol. 50, Apr. 15, 2011 (Apr. 15, 2011), pp. 4601-4605, XP002737689, ISSN: 1433-7851.
Sadik Mohamed Metal: Scaling Relationship and Optimization of Double-Pulse Electroporation, Biophysical Journal, vol. 106, No. 4, Feb. 2014 (Feb. 2014), pp. 801-812, XP028615252, ISSN: 0006-3495.
Written Opinion of the International Preliminary Examining Authority (IPEA) dated Feb. 16, 2017.
International Preliminary Report on Patentability dated Mar. 28, 2017.
As-Filed Chapter II Demand filed on Oct. 28, 2016.

PROCESS FOR MANUFACTURING ETHYLENE OXIDE USING SCALED SELECTIVITY VALUES

TECHNICAL FIELD

This disclosure relates generally to processes for making ethylene oxides, and more specifically, to a method and system of using scaled selectivity values to eliminate or reduce the deviation from optimum operation when the value of an ethylene oxide production parameter is changed.

BACKGROUND

This disclosure relates to a process for manufacturing ethylene oxide. Ethylene oxide is used to produce ethylene glycol, which is used as an automotive coolant, as antifreeze, and in preparing polyester fibers and resins, nonionic surfactants, glycol ethers, ethanolamines, and polyethylene polyether polyols.

The production of ethylene oxide generally occurs via the catalytic epoxidation of ethylene in the presence of oxygen. Conventional silver-based catalysts used in such processes provide a relatively lower efficiency or "selectivity" (i.e., a lower percentage of the reacted ethylene is converted to the desired ethylene oxide). In certain exemplary processes, when using conventional catalysts in the epoxidation of ethylene, the theoretically maximal selectivity towards ethylene oxide, expressed as a fraction of the ethylene converted, does not reach values above the 6/7 or 85.7 percent limit. Therefore, this limit had long been considered to be the theoretically maximal selectivity of this reaction, based on the stoichiometry of the following reaction equation:

cf. Kirk-Othmer's Encyclopedia of Chemical Technology, 4th ed., Vol. No. 9, 1994, p. 926.

Certain "high efficiency" or "high selectivity" silver-based catalysts are highly selective towards ethylene oxide production. For example, when using certain catalysts in the epoxidation of ethylene, the theoretically maximal selectivity towards ethylene oxide can reach values above the 6/7 or 85.7 percent limit referred to, for example 88 percent, or 89 percent, or above. High selectivity catalysts comprise as their active components silver, rhenium, and at least one further metal. See EP0352850B1 and WO2007/123932.

All silver-based catalysts used in ethylene oxide production processes are subject to an aging-related performance decline during normal operation, and they need to be exchanged periodically. The aging manifests itself by a reduction in the activity of the catalyst and may also manifest itself by a reduction in selectivity. Usually, when a reduction in catalyst activity occurs, the reaction temperature is increased in order to maintain a constant ethylene oxide production rate. The reaction temperature may be increased until it reaches the design limit or becomes undesirably high, or the selectivity may become undesirably low, at which point in time the catalyst is deemed to be at the end of its lifetime and would need to be exchanged or regenerated. Current industry practice is to discharge and replace the catalyst when it is at the end of its useful life.

Conventional catalysts have relatively flat selectivity curves with respect to the gas phase promoter concentration in the feed, i.e., the selectivity is almost invariant (i.e., the change in selectivity with respect to a change in gas phase promoter concentration in the feed is less than about 0.1%/ppmv) over a wide range of such promoter concentrations, and this invariance is substantially unaltered as reaction temperature is changed during prolonged operation of the catalyst. However, conventional catalysts have nearly linear activity decline curves with respect to the gas phase promoter concentration in the feed, i.e., with increasing gas phase promoter concentration in the feed, temperature has to be increased or the ethylene oxide production rate will be reduced. Therefore, when using a conventional catalyst, for optimum selectivity, the gas phase promoter concentration in the feed can be chosen at a level at which the maximum selectivity can be maintained at relatively lower operating temperatures. Typically, the gas phase promoter concentration can remain substantially the same during the entire lifetime of a conventional catalyst. On the other hand, the reaction temperature may be adjusted to obtain a desired production rate without any substantial impact on selectivity due to non-optimal gas phase promoter concentration.

By contrast, high selectivity catalysts tend to exhibit relatively steep selectivity curves as a function of gas phase promoter concentration as the concentration moves away from the value that provides the highest selectivity (i.e., the change in selectivity with respect to a change in gas phase promoter concentration is at least about 0.2%/ppmv when operating away from the selectivity maximizing promoter concentration). Thus, small changes in the promoter concentration can result in significant selectivity changes, and the selectivity exhibits a pronounced maximum, i.e. an optimum, at certain concentrations (or feed rates) of the gas phase promoter, when reactor pressure and feed gas composition are kept unchanged for a given reaction temperature and catalyst age.

For a high selectivity catalyst, at any given production rate and set of operating conditions, a temperature (T) and overall catalyst chloriding effectiveness ($Z^*$) combination exists that results in optimum actual selectivity. As the catalyst ages, for a fixed production rate target, temperature (T) and $Z^*$ are increased to maintain activity, meet the production rate target, and achieve optimum selectivity. At a constant production rate, the general practice is to monitor actual selectivity response with $Z^*$ and optimize it. However, when an ethylene oxide plant operates at varying production rates, determining whether the catalyst has reached optimal selectivity is challenging.

There is a need for keeping the ethylene oxide process operating at optimal selectivity as changes are made to the value of an ethylene oxide production parameter.

SUMMARY

In accordance with a first aspect of the present disclosure, a method of operating a process for producing ethylene oxide by reacting a feed gas comprising ethylene, oxygen, and at least one organic chloride over a high selectivity, silver-based catalyst comprising rhenium using scaled selectivity values is provided. The method comprises the steps of operating the process at a first value of a reaction temperature, a first value of an overall catalyst chloriding effectiveness, and a first set of values for a set of reference operating conditions, the set of reference operating conditions comprising a plurality of reference reaction parameters, to yield a first value of a target ethylene oxide production parameter and a first actual selectivity value. The method also comprises operating the process at a second value of the reaction temperature, a second value of the overall catalyst chloriding effectiveness, and a second set of values for the set of reference operating conditions, to yield a second value of the target ethylene oxide production parameter and a second actual selectivity value. The method further comprises calculating a scaled second selectivity value from the second actual selectivity value, a value in the second set of values of at least one of the reference operating conditions in the set of reference operating conditions, and a reference value of the at least one of the reference operating conditions in the set of reference operating conditions. In addition, a determination is made that an adjustment is required to at least one of the reaction temperature and the overall catalyst chloriding effectiveness based on the scaled second selectivity value and the first actual selectivity value. The method comprises subsequently adjusting at least one of the reaction temperature to a third reaction temperature value and/or the overall catalyst chloriding effectiveness to a third overall catalyst chloriding effectiveness value, such that the scaled selectivity increases. In certain examples, the method further comprises calculating a scaled first selectivity value from the first actual selectivity value, a value in the first set of values of the at least one of the reference operating conditions in the set of reference operating conditions, and the reference value of the at least one of the reference operating conditions in the set of reference operating conditions, wherein the step of determining that an adjustment is required to at least one of the reaction temperature and the overall catalyst chloriding effectiveness is based on the scaled second selectivity value and the scaled first selectivity value.

In accordance with a second aspect of the disclosure, a method of operating a process for producing ethylene oxide by reacting a feed gas comprising ethylene, oxygen, and at least one organic chloride over a high selectivity, silver-based catalyst comprising rhenium using scaled selectivity values and scaled reaction temperature values is provided. The method comprises operating the process at a first value of a reaction temperature, a first value of an overall catalyst chloriding effectiveness, and a first set of values for a set of reference operating conditions, the set of reference operating conditions comprising a plurality of reference reaction parameters, to yield a first value of a target ethylene oxide production parameter and a first actual selectivity value. The method further comprises subsequently operating the process at a second value of the reaction temperature, a second value of the overall catalyst chloriding effectiveness, and a second set of values for the set of reference operating conditions, to yield a second value of the target ethylene oxide production parameter and a second actual selectivity value. The method also comprises calculating a scaled first selectivity value from the first actual selectivity value, a value in the first set of values of a first at least one of the reference operating conditions in the set of reference operating conditions, and a reference value of the first at least one of the reference operating conditions in the set of reference operating conditions, as well as calculating a scaled second selectivity value from the second actual selectivity value, a value in the second set of values of the first at least one of the reference operating conditions in the set of reference operating conditions, and the reference value of the first at least one of the reference operating conditions in the set of reference operating conditions. In addition, the method comprises calculating a scaled first reaction temperature value from the first value of the reaction temperature, a value in the first set of values of a second at least one of the reference operating conditions in the set of reference operating conditions, and a reference value of the second at least one of the reference operating conditions in the set of reference operating conditions, as well as calculating a scaled second reaction temperature value from the second value of the reaction temperature, a value in the second set of values of the second at least one of the reference operating conditions in the set of reference operating conditions, and the reference value of the second at least one of the reference operating conditions in the set of reference operating conditions. A determination is made that an adjustment is required to at least one of the reaction temperature and the overall catalyst chloriding effectiveness by comparing the scaled first selectivity to the scaled second selectivity. The method comprises subsequently adjusting at least one of the reaction temperature to a third reaction temperature value and the overall catalyst chloriding effectiveness to a third overall catalyst chloriding effectiveness value such that the scaled selectivity increases, wherein the step of subsequently adjusting is based on the first scaled selectivity value, the second scaled selectivity value, the first scaled reaction temperature, and the second scaled reaction temperature.

DETAILED DESCRIPTION

Figure 1:
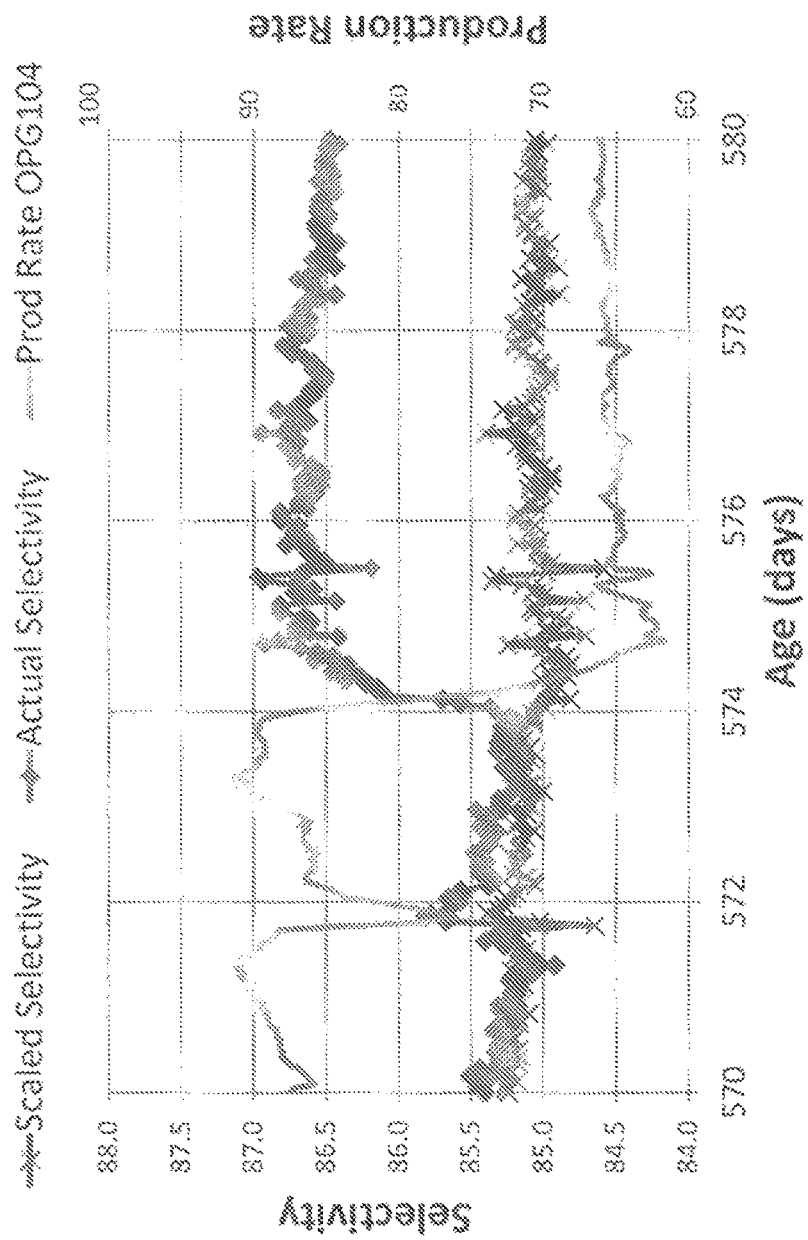
FIG. 1 depicts a plot of the scaled selectivity, actual selectivity, and production rate for a high selectivity silver-based catalyst comprising rhenium for a 10 day period.

The present disclosure provides methods of operating a process for producing ethylene oxide by reacting ethylene, oxygen, and at least one organic chloride over a high-efficiency catalyst. The method uses scaled selectivity values to determine when a change in operating conditions made to adjust the value of a target ethylene oxide production parameter has caused to the process to move farther away from optimal operation. As a result, the methods described herein beneficially avoid the need to conduct a full optimization study to determine if the adjusted value of the ethylene oxide production parameter has adversely impacted the process relative to a desired optimum.

The present specification provides certain definitions to guide those of ordinary skill in the art in the practice of the present invention. Provision, or lack of provision, of a definition for a particular term or phrase is not meant to imply any particular importance, or lack thereof; rather, and unless otherwise noted, terms are to be understood according to the conventional usage by those of ordinary skill in the relevant art. Unless defined otherwise, technical and scientific terms used herein have the same meaning as commonly understood by one of skill in the art to which this invention belongs.

A supported catalyst for ethylene oxide manufacture should have acceptable activity, selectivity, and stability. One measure of the useful life of a catalyst is the length of time that reactants can be passed through the reaction system during which time acceptable productivity is obtained in light of all relevant factors.

The "activity" of a catalyst in a fixed bed reactor is generally defined as the reaction rate towards the desired product per unit of catalyst volume in the reactor. The activity of a catalyst can be quantified in a number of ways, one being the mole percent of ethylene oxide contained in the outlet stream of the reactor relative to that in the inlet stream (the mole percent of ethylene oxide in the inlet stream typically, but not necessarily, approaches zero percent) while the reaction temperature is maintained substantially constant; and another being the temperature required to maintain a given rate of ethylene oxide production. In many instances, activity is measured over a period of time in terms of the mole percent of ethylene oxide produced at a specified constant temperature. Alternatively, activity may be measured as a function of the temperature used to sustain production of a specified constant mole percent of ethylene oxide.

The "efficiency" of the oxidation, which is synonymous with "selectivity," refers to the relative amount (as a fraction or in percent) of converted or reacted ethylene that forms a particular product. For example, the "selectivity to ethylene oxide" refers to the percentage on a molar basis of converted ethylene that forms ethylene oxide. "Actual selectivity" means the percentage on a molar basis of converted ethylene that forms ethylene oxide at an actual set of operating conditions at which an ethylene oxide process is operated. In contrast, "scaled selectivity" refers to an actual selectivity that has been scaled (i.e. adjusted) to correspond to values of a set of reference operating conditions which may differ from those that yielded the actual selectivity.

The term "ethylene oxide production parameter" is used herein to describe a variable that relates to the extent to which ethylene oxide is produced. Examples of ethylene oxide production parameters include ethylene oxide concentration, ethylene oxide yield, ethylene oxide production rate, ethylene oxide production rate/catalyst volume, ethylene conversion, and oxygen conversion. Thus, the ethylene oxide concentration relates to the ethylene oxide production rate because the production rate may be obtained by multiplying the ethylene oxide concentration and the net product flow rate from the reactor. The ethylene oxide production rate/catalyst volume may be determined by dividing the production rate by the volume of the catalyst bed. The oxygen and ethylene conversions are related to the production of the ethylene oxide by the selectivity. Selectivity and activity are not ethylene oxide production parameters. A "target ethylene oxide production parameter" is an ethylene oxide production parameter that is used as a specification for operating an ethylene oxide process. In one example, an ethylene oxide process is operated to achieve a specified value of an ethylene oxide production rate, in which case the ethylene oxide production rate would be considered a target ethylene oxide production parameter.

"Chloride-removing hydrocarbons" means hydrocarbons lacking chloride atoms. These are believed to strip or remove chlorides from the catalyst. Examples include paraffinic compounds such as ethane and propane as well as olefins such as ethylene and propylene.

"ΔEO", also referred to as "delta EO" or "ΔEO %", is the difference between the outlet and inlet ethylene oxide concentrations, corrected for the change in molar volume across the reactor, measured in mole percent. It is calculated from the reactor inlet and outlet concentrations in mole percent of ethylene oxide ($EO_{inlet}$ and $EO_{outlet}$, respectively) as follows: $\Delta EO\% = SF*EO_{outlet} - EO_{inlet}$. The term "SF" or "Shrink Factor" represents the net volumetric reduction occurring due to the production of the ethylene oxide. For every mole of ethylene oxide produced, there is a net reduction of 0.5 moles of total gas resulting in a corresponding reduction in the volumetric flow rate. The SF is typically calculated as follows: $(200+EO_{inlet})/(200+EO_{outlet})$, where $EO_{inlet}$ and $EO_{outlet}$ are the concentrations in mole percent of ethylene oxide in the reactor inlet and outlet gas mixtures, respectively.

"Gas phase promoters" means compounds that enhance the selectivity and/or activity of a process for the production of ethylene oxide. Preferred gas phase promoters include organic chlorides. More preferably, the gas phase promoter is at least one selected from the group consisting of methyl chloride, ethyl chloride, ethylene dichloride, vinyl chloride, and mixtures thereof. Ethyl chloride and ethylene dichloride are most preferred as the gas phase promoter fed into the process.

The terms "high efficiency catalyst" and "high selectivity catalyst" refer to a catalyst that is capable of producing ethylene oxide from the ethylene and oxygen at a selectivity greater than 85.7 percent. The observed actual selectivity of a high selectivity catalyst may fall below 85.7 percent under certain conditions based on process variables, catalyst age, and the like. However, if the catalyst is capable of achieving at least an 85.7 percent selectivity, at any point during its life, for example, under any set of reaction conditions, or by extrapolating lower efficiencies observed at two different oxygen conversions obtained by varying gas hourly space velocity to the limiting case of zero oxygen conversion, it is considered to be a high selectivity catalyst.

"Overall catalyst chloriding effectiveness" means the net effect of the promoting and non-promoting gas phase species in chloriding the catalyst. The catalyst chlorination state, i.e., the ultimate coverage of chlorides on the surface of the catalyst, will depend on at least the overall catalyst chloriding effectiveness and the catalyst temperature. An "overall catalyst chloriding effectiveness value" is a numeric value indicative of the overall catalyst chloriding effectiveness. In the case of organic gas-phase promoters, an overall catalyst chloriding effectiveness value can be defined as the dimensionless quantity $Z^*$ and represented by the following formula:

$$Z^* = \frac{\text{ethyl chloride equivalent } (ppmv)}{\text{ethane equivalent (mole percent)}} \qquad (1)$$

wherein the ethyl chloride equivalent is the concentration in ppmv (which is equivalent to ppm mole for an ideal gas) of ethyl chloride that provides substantially the same catalyst chloriding effectiveness of the organic chlorides present in reactor feed stream 8 (See FIG. 2) at the concentrations of the organic chlorides in feed stream 8; and the ethane equivalent is the concentration of ethane in mole percent that provides substantially the same catalyst dechloriding effectiveness of the non-chloride containing hydrocarbons in the reactor feed stream 8 at the concentrations of the non-chloride containing hydrocarbons in the reactor feed stream 8. Further explanation of the "overall catalyst chloriding value" is provided in U.S. Pat. Nos. 8,389,751 and 8,362,284.

The term "operating conditions", as used herein, refers to reaction parameters that include reactor inlet pressure, reactor outlet pressure, gas hourly space velocity; composition of the reactor feed stream, concentrations of components in the reactor feed stream, composition of the reactor product stream, average compositions of components taken along the catalyst bed, average pressure along the catalyst bed, concentrations of components in the reactor product stream, and any of the ethylene oxide production parameters (as defined above). For purposes of this disclosure and the calculation of scaled selectivity and scaled reaction temperature values, the term "operating conditions" does not include reaction temperature, overall catalyst chloriding effectiveness, selectivity, or activity.

"Reaction temperature," or "(T)" refers to any selected temperature(s) that are directly or indirectly indicative of the catalyst bed temperature. In certain embodiments, the reaction temperature may be a catalyst bed temperature at a specific location in the catalyst bed. In other embodiments, the reaction temperature may be a numerical average of several catalyst bed temperature measurements made along one or more catalyst bed dimensions (e.g., along the length). In additional embodiments, the reaction temperature may be the reactor outlet gas temperature. In further embodiments, the reaction temperature may be the reactor coolant outlet temperature. In other embodiments, the reaction temperature may be the reactor coolant inlet temperature. A "scaled reaction temperature" is a reaction temperature that has been scaled (i.e. adjusted) to correspond to values of a set of reference operating conditions which may differ from those at which the reaction temperature was observed. The specific temperature measurements used to calculate scaled selectivity values and scaled reaction temperature values need not be the same temperatures that are manipulated in controlling the ethylene oxide process, even though both would be considered "reaction temperatures" as defined herein. For example, scaled selectivity values may be calculated based on reactor outlet gas temperature measurements while the reactor coolant inlet temperature may be the manipulated "reaction temperature."

The term "optimum" when used herein to describe an ethylene oxide process employing a high selectivity catalyst refers to a combination of values of reaction temperature and overall catalyst chloriding effectiveness that yields a maximum value for selectivity at a target value of a selected ethylene oxide production parameter while holding constant all of an ethylene concentration, an oxygen concentration, a carbon dioxide concentration, a reactor pressure, and a gas hourly space velocity, wherein each of the conditions may be measured as a reactor inlet, reactor outlet, or average catalyst bed value.

"Reference operating conditions" refers to operating conditions that may be used to scale actual selectivity or actual reaction temperature. In practice, the reference values used for the reference operating conditions need never be the actual values for the reference operating conditions. Instead, they provide a common basis for comparing observed selectivities and reaction temperatures corresponding to different values of a target ethylene oxide production parameter. For any set or sets of operating conditions, the particular reference operating conditions used to calculate a scaled selectivity value need not be the same as the reference operating conditions used to calculate a scaled reaction temperature value. For example, at two different sets of operating conditions, the corresponding scaled selectivities may be calculated using ethylene oxide production rate and the inlet carbon dioxide concentration, wherein the corresponding scaled reaction temperatures may be calculated using $\Delta EO$ and reactor pressure. For purposes of this disclosure and the calculation of scaled selectivity and scaled reaction temperature values, the term "reference operating conditions" does not include reaction temperature, overall catalyst chloriding effectiveness, selectivity, or activity.

High selectivity silver-based catalysts comprising rhenium and methods of making them are known to those of skill in the art. See EP0352850B1, WO2007/123932, WO2014/150669, EP1613428, or CN102133544.

Suitable reactors for the epoxidation reaction include fixed bed reactors, fixed bed tubular reactors, continuous stirred tank reactors (CSTR), fluid bed reactors and a wide variety of reactors that are well known to those skilled in the art. The desirability of recycling unreacted feed, or employing a single-pass system, or using successive reactions to increase ethylene conversion by employing reactors in series arrangement can also be readily determined by those skilled in the art. The epoxidation reaction is carried out at a temperature that is preferably at least about 200° C., more preferably at least about 210° C., and most preferably at least about 220° C. Reaction temperatures of no more than about 300° C. are preferred, more preferably not more than about 290° C., and most preferably not more than about 280° C.

The reactor pressure is selected based on the desired mass velocity and productivity and ranges generally from about 5 atm (506 kPa) to about 30 atm (3.0 MPa). The gas hourly space velocity (GHSV) is preferably greater than about 3,000 hr$^{-1}$, more preferably greater than about 4,000 hr$^{-1}$, and most preferably greater than about 5,000 hr$^{-1}$.

Figure 2:
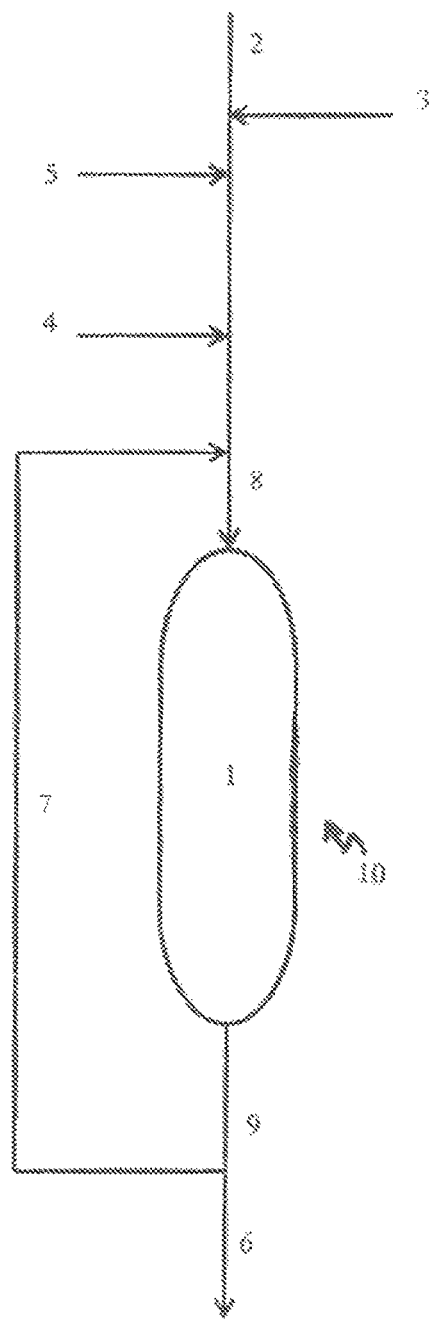
FIG. 2 is a process flow diagram depicting an embodiment of a process for making ethylene oxide by epoxidizing ethylene over a high selectivity silver-based catalyst comprising rhenium.

FIG. 2 is a process flow diagram depicting an embodiment of a process for making ethylene oxide by epoxidizing ethylene over a high selectivity silver-based catalyst comprising rhenium. Process 10 includes a reactor 1 comprising multiple reactor tubes with a high selectivity catalyst therein. Ethylene feed stream 2 (which may also include saturated hydrocarbons, such as ethane as an impurity) is combined with ballast gas 3, oxygen feed 5, and gas phase promoter feed 4 to define the reactor feed gas inlet stream 8, proximate to the reactor inlet. The reactor product stream 9 includes the ethylene oxide product in addition to side products (e.g., carbon dioxide, water and small amounts of saturated hydrocarbons), unreacted ethylene, oxygen, and inert gases. In commercial processes, the ethylene oxide product along with some water product is removed from the reactor product stream 9 in an ethylene oxide recovery unit (not shown). If desired, a recycle stream 7 may also be provided to recycle the unreacted ethylene and oxygen, in which case a net product stream 6 is also provided. However, if a recycle stream 7 is provided, a purge line is preferably provided to reduce the build-up of impurities and/or side products such as argon and ethane. In addition, commercial processes also include a carbon dioxide removal step that is performed upstream of where recycle stream 7 combines with the fresh feed and enters the reactor 1. Recycle stream 7 also comprises carbon dioxide.

Oxygen feed 5 may comprise substantially pure oxygen or air. If pure oxygen is used, ballast gases or diluents such as nitrogen or methane may also be included to maintain the oxygen concentration below a maximum level allowed because of flammability considerations. Generally, the oxygen concentration in reactor feed 8 will be at least about 1 mole percent and preferably at least about 2 mole percent. The oxygen concentration will generally be no more than about 15 mole percent and preferably no more than about twelve (12) mole percent. The ballast gas 3 (e.g., nitrogen or methane) is generally from about 50 mole percent to about 80 mole percent of the total composition of reactor feed stream 8.

The concentration of ethylene in reactor feed stream 8 may be at least about 18 mole percent and more preferably at least about 20 mole percent. The concentration of ethylene in reactor feed stream 8 is preferably no greater than about 50 mole percent, and more preferably is no greater than about 40 mole percent.

When present, the carbon dioxide concentration in reactor feed stream 8 has an adverse effect on the selectivity, activity and/or stability of catalysts used in reactor 1. Carbon dioxide is produced as a reaction by-product and may also be introduced with other inlet reaction gases as an impurity. In commercial ethylene epoxidation processes, at least a part of the carbon dioxide is removed continuously in order to control its concentration to an acceptable level in the cycle. The carbon dioxide concentration in reactor feed 8 is generally no more than about 8 mole percent, preferably no more than about 4 mole percent, and even more preferably no more than about 2 mole percent of the total composition of reactor feed 8. Water may also be present in the feed gas stream in a concentration that is up to 2 mole percent.

In an embodiment, the preferred concentration of ethane in the reactor feed 8, when present, is up to about 2 mole percent.

For a high selectivity catalyst, at a given catalyst age, a fixed value of a target ethylene oxide production parameter and fixed values of an ethylene concentration, an oxygen concentration, a carbon dioxide concentration, a reactor pressure, and a gas hourly space velocity (wherein each of the conditions may be measured as a reactor inlet, reactor outlet, or average catalyst bed value), there exists a combination of a reaction temperature value and an overall catalyst chloriding effectiveness value that provides an optimum (maximum) actual selectivity. For example, in some commercial plants, the practice is to operate the process at a desired value of a selected target ethylene oxide production parameter using a combination of a reaction temperature value and an overall catalyst chloriding effectiveness value which maximizes selectivity.

However, as plant economics and/or operating goals change, the desired value of the selected target ethylene oxide production parameter may change. For example, a desired value of an ethylene oxide production rate may change. The change may be effected by changing the value of reaction temperature, overall catalyst chloriding effectiveness, and/or one or more operating conditions (as defined herein). However, the optimum selectivity value varies with at least the value of ethylene oxide production parameters. In known processes, when the desired value of a target ethylene oxide production parameter is changed, a re-optimization is often required in which reaction temperature and overall catalyst chloriding effectiveness must be varied (often without knowing in which directions they should be varied) until selectivity is maximized, while still maintaining the new desired value of the target ethylene oxide production parameter. If, as it happens, the process is already at or close to optimum at the new value of the target ethylene oxide production parameter, this re-optimization may be unnecessary and may introduce undesirable process disturbances. Thus, in general, it is desirable to know whether the actual selectivity at the new value of a target ethylene oxide production parameter is optimal, or at least no less optimal, than the actual selectivity at the original value of the selected target ethylene oxide parameter.

As explained further below, the method of the present disclosure provides for the calculation of "scaled selectivities" that allow actual selectivities obtained at different values of an ethylene oxide production parameter (and different values of other operating conditions) to be scaled to a common set of reference operating conditions. Thus, scaled selectivities may be compared to determine if the process has moved away from the optimum selectivity that is applicable to the new value of an ethylene oxide production parameter without actually performing an optimization to determine what the optimum value is. The comparison can thus be used to determine whether re-optimization at the new value of the ethylene oxide production parameter is desirable or necessary. In addition, scaled selectivities may reveal that the process was not optimized at the original value of an ethylene oxide production parameter. In that case, even if the scaled selectivity at the new target value indicates that the process is relatively better optimized than before, re-optimization may still be desirable.

If scaled selectivity values reveal that re-optimization is warranted, it is generally the case that they alone will not indicate in which directions (increase or decrease) reaction temperature and/or overall catalyst chloriding effectiveness should be changed. In some cases, in order to maintain a desired value of an ethylene oxide production parameter, any changes made to reaction temperature and overall catalyst chloriding effectiveness to increase the actual selectivity will have to be made in opposite directions (e.g. if temperature is increased, overall catalyst chloriding effectiveness is either not changed or is decreased). The use of scaled reaction temperature values in combination with scaled selectivity values provides additional information about the directions in which reaction temperature and/or overall catalyst chloriding effectiveness should be changed to increase selectivity while maintaining the desired value of an ethylene oxide production parameter.

In summary, scaled selectivity is a tool for determining if selectivity is at optimum after one or more operating conditions are changed, and, if the scaled selectivity is not at optimum, provides a target for returning to optimum selectivity. Scaled selectivity values are calculated by adjusting actual selectivity values to account for the effects of differences between the actual values and reference values for at least one reference operating condition in a set of reference operating conditions. After determining the scaled selectivity after a change in operating conditions, the need for additional adjustments to maximize the scaled selectivity can be identified. While over a long period of operation some aging-related decline in catalyst selectivity is expected, as shown in FIG. 1, on a short-term basis, e.g., 0-7 days, when the value of an ethylene oxide production parameter (which is the ethylene oxide production rate in FIG. 1) changes, the scaled selectivity can be maintained constant within the accuracy of the scaled selectivity equation and the limits of plant operations and analytical measurements.

Scaled selectivity values at a given value of a target ethylene oxide production parameter may be calculated using a variety of different scaling relationships and may be represented by the following general formula:

$$Es = f(E, x_1 \ldots x_n, x_{1r} \ldots x_{nr}) \tag{2}$$

wherein, $x_1 \ldots x_n$ is a set of values for a set of reference operating conditions 1 to n, $x_{1r} \ldots x_{nr}$ is a set of reference values for the set of reference conditions 1 to n, E=the actual selectivity corresponding to the set of values $x_1 \ldots x_n$, and Es is the scaled selectivity for the set of values $x_1 \ldots x_n$ of reference operating conditions 1 to n.

Similarly, scaled reaction temperatures at a given value of a target ethylene oxide production parameter may be calculated using a variety of different scaling relationships and may be represented by the following general formula:

$$Ts = f(T, x_1 \ldots x_n, x_{1r} \ldots x_{nr}) \quad (3)$$

wherein, $x_1 \ldots x_n$ is a set of values for a set of reference operating conditions 1 to n, $x_{1r} \ldots x_{nr}$ is a set of reference values for the set of reference conditions 1 to n, T=the reaction temperature corresponding to the set of values $x_1 \ldots x_n$, and Ts is the scaled reaction temperature for the set of values $x_1 \ldots x_n$, of reference operating conditions 1 to n.

The scaling relationships that define the function $f$ in equations (2) and (3) may be linear or non-linear. Linear relationships may be linear proportional or linear non-proportional. In certain examples, the following relationship may be used to calculate scaled selectivity values for two different sets of operating conditions, j=1 and 2:

$$E_{S_j} = E_j + \sum_{i=1}^{n} \frac{dE}{dx_i}(x_{ir} - x_{ij}) \quad (4)$$

wherein, j is an index that takes a value of 1 for the step of operating the process at a first value of a reaction temperature, a first value of an overall catalyst chloriding effectiveness, and a first set of values for a set of reference operating conditions, and which takes a value of 2 for the step of subsequently operating the process at a second value of the reaction temperature, a second value of the overall catalyst chloriding effectiveness, and a second set of values for the set of reference operating conditions, $E_{sj}$ is the scaled jth selectivity value (%), $E_j$ is the jth actual selectivity value (%), $x_{ij}$ is the value in the jth set of values of the ith reference operating condition from the at least one of the reference operating conditions in the set of reference operating conditions, $x_{ir}$ is the reference value of the ith reference operating condition from the at least one of the reference operating conditions in the set of reference operating conditions, $x_i$ is the ith reference operating condition from the at least one of the reference operating conditions in the set of reference operating conditions, i is an index corresponding to a reference operating condition from the at least one of the reference operating conditions in the set of reference operating conditions, n is an index indicative of the total number of reference operating conditions comprising the at least one of the reference operating conditions in the set of reference operating conditions, and $dE/dx_i$ is the first derivative of selectivity with respect to the ith reference operating condition from the at least one of the reference operating conditions in the set of reference operating conditions.

Values of $dE/dx_i$ may be determined from plant or laboratory data points at different values of $x_i$ where reaction temperature T and overall catalyst chloriding effectiveness (e.g., Z*) are at optimum for each data point. In the simplest implementation, the values of $dE/dx_i$ are determined one at a time as the value of $x_i$ is changed while the values of the other reference operating conditions x are held constant. Other operating conditions not included in the set of reference operating conditions should also be held constant especially if they affect selectivity. This method assumes that $dE/dx_i$ is only affected by $x_i$ and not one or more of the other x values. In another implementation, more than one (or all) of the $dE/dx_i$ values can be determined at the same time from designed or undesigned data where more than one reference operating condition x may be changed at the same time. Suitable methods for designing the experiments, mining undesigned data, and curve-fitting are known by those skilled in the art. The value of $dE/dx_i$ may be a constant or may be a function of the value of $x_i$ or any other reference operating condition x.

In certain examples, the following relationship may be used to calculate scaled reaction temperature values for two different sets of operating conditions, j=1 and 2:

$$T_{s_j} = T_j + \sum_{i=1}^{n} \frac{dT}{dx_i}(x_{ir} - x_{ij}) \quad (5)$$

wherein, j is an index that takes a value of 1 for the step of operating the process at a first value of a reaction temperature, a first value of an overall catalyst chloriding effectiveness, and a first set of values for a set of reference operating conditions, and which takes a value of 2 for the step of subsequently operating the process at a second value of the reaction temperature, a second value of the overall catalyst chloriding effectiveness, and a second set of values for the set of reference operating conditions, $Ts_j$ is the scaled jth reaction temperature value (° C.), $T_j$ is the jth reaction temperature value (° C.), $x_{ij}$ is the value in the jth set of values of the ith reference operating condition from the at least one of the reference operating conditions in the set of reference operating conditions, $x_{ir}$ is the reference value of the ith reference operating condition from the at least one of the reference operating conditions in the set of reference operating conditions, $x_i$ is the ith reference operating condition from the at least one of the reference operating conditions in the set of reference operating conditions, i is an index corresponding to a reference operating condition from the at least one of the reference operating conditions in the set of reference operating conditions, n is an index indicative of the total number of reference operating conditions in the at least one of the reference operating conditions in the set of reference operating conditions, and $dT/dx_i$ is the first derivative of reaction temperature with respect to the ith reference operating condition from the at least one of the reference operating conditions in the set of reference operating conditions.

Values of $dT/dx_i$ may be determined from plant or laboratory data points at different values of $x_i$ where reaction temperature T and overall catalyst chloriding effectiveness (e.g., Z*) are at optimum for each data point. In the simplest implementation, the values of $dT/dx_i$ are determined one at a time as the value of $x_i$ is changed while the values of other reference operating conditions x are held constant. Other operating conditions not included in the set of reference operating conditions should also be held constant, especially if they affect reaction temperature. This method assumes that $dT/dx_i$ is only affected by xi and not one or more of the other x values. In another implementation, more than one (or all) of the $dT/dx_i$ values can be determined at the same time from designed or undesigned data where more than one reference operating condition x may be changed at the same time. Suitable methods for designing the experiments, mining undesigned data, and curve-fitting are known by those skilled in the art. The value of $dT/dx_i$ may be a constant or may be a function of the value of $x_i$ or the any other reference operating conditions x.

In any given application of the methods herein, the scaling relationships used to calculate scaled selectivity $E_s$ and scaled reaction temperature $T_s$ may be different or the same. Moreover, the particular set of reference operating conditions 1 to n used to calculate scaled selectivity $E_s$ and scaled reaction temperature $T_s$ may be the same, partially overlapping, or not partially overlapping. In each case, at least one reference operating condition is used to calculate scaled selectivity $E_s$ and scaled reaction temperature $T_s$. It is convenient to use the phrase "set of reference operating conditions" to refer to an entire set of reference operating conditions that may be defined and potentially used to calculate scaled selectivities or reaction temperatures. In certain portions of the disclosure, the reference condition(s) used to calculate scaled selectivity are distinguished from those used to calculate scaled reaction temperature by using the phrases "a first at least one of the reference operating conditions" and "a second at least one of the reference operating conditions." For example, in equations (2) and (4) the values $x_1$ to $x_n$ and $x_{1j}$ to $x_{nj}$, respectively, may be described as the values of "a first at least one of the reference operating conditions in the set of reference operating conditions," and in the equations (3) and (5) the values of $x_1$ to $x_n$ and $x_{1j}$ to $x_{nj}$, respectively, may be described as the values of "a second at least one of the reference operating conditions in the set of reference operating conditions." The values of n may also be different when using equations (4) and (5) to calculate scaled selectivity values and scaled reaction temperature values.

Scaled selectivity values calculated for different actual operating conditions may be compared to one another in a variety of different ways to determine if re-optimization is warranted. Examples include differences, absolute values of differences, ratios, and combinations thereof. Scaled reaction temperature values calculated for different actual operating conditions may be compared to one another using similar techniques to determine if the directions in which to change reaction temperature and/or overall catalyst chloriding effectiveness in order to restore or move closer to optimal operation.

In accordance with one method, the absolute value of a difference between scaled selectivities is calculated and compared to a selected value to determine if re-optimization is warranted:

$$|E_{S2}-E_{S1}|>\Delta E_{Smax} \quad (6)$$

wherein, $E_{S1}$ is a scaled selectivity (%) calculated based on the value in a first set of values of at least one of the reference operating conditions in a set of reference operating conditions and a reference value of the at least one of the reference operating conditions in the set of reference operating conditions, $E_{S2}$ is a scaled selectivity (%) calculated based on the value in a second set of values of the at least one of the reference operating conditions in the set of reference operating conditions and the reference value of the at least one of the reference operating conditions in the set of reference operating conditions, and $\Delta E_{Smax}$ is a selected maximum (%) of the absolute value of the difference of scaled selectivities used to determine whether adjustment to the values of reaction temperature and/or overall catalyst chloriding effectiveness is warranted.

In certain examples, reaction temperature and/or overall catalyst chloriding effectiveness are only adjusted if the inequality in equation (6) is satisfied and if $E_{S2}$ is less than $E_{S1}$, wherein the second set of actual operating conditions corresponding to $E_{S2}$ is maintained after the first set of actual operating conditions corresponding to $E_{S1}$. When the inequality in equation (6) is satisfied and the scaled selectivity has decreased after making a change from the first set of values of a set of reference operating conditions to the second set of values of the set of reference operating conditions, the process has moved farther away from optimum. Thus, it is desirable to restore the process to an actual selectivity that corresponds to a scaled selectivity substantially equal to $E_{S1}$ to keep the process operating at optimum (if it was optimized at the first set of operating conditions) or to at least maintain the degree of optimization of the first set of operating conditions. In accordance with such examples, no adjustments are made to reaction temperature and/or overall catalyst chloriding effectiveness if equation (6) is satisfied and $E_{S2}$ is greater than $E_{S1}$. Preferred values of $\Delta E_{Smax}$ will depend on the accuracy and reliability of the measurements and model used to determine scaled selectivity values. The value of $\Delta E_{Smax}$ is preferably set no lower than the reliability of reference operating condition measurements and the scaled selectivity model will allow. In certain examples, $\Delta E_{Smax}$ is from about 0.1 to about 0.3 percentage points. However, the value could be higher.

In other examples, if equation (6) is satisfied, reaction temperature and/or overall catalyst chloriding effectiveness may be adjusted even if the scaled selectivity has increased as a result of changing the process from the first set of operating conditions to the second set of operating conditions. When equation (6) is satisfied and scaled selectivity increases, the process was not operating at an optimum prior to the change in operating conditions. Thus, while the change moved the process toward optimum, it may have been at a significantly sub-optimum point of operation to begin with.

Figure 3:
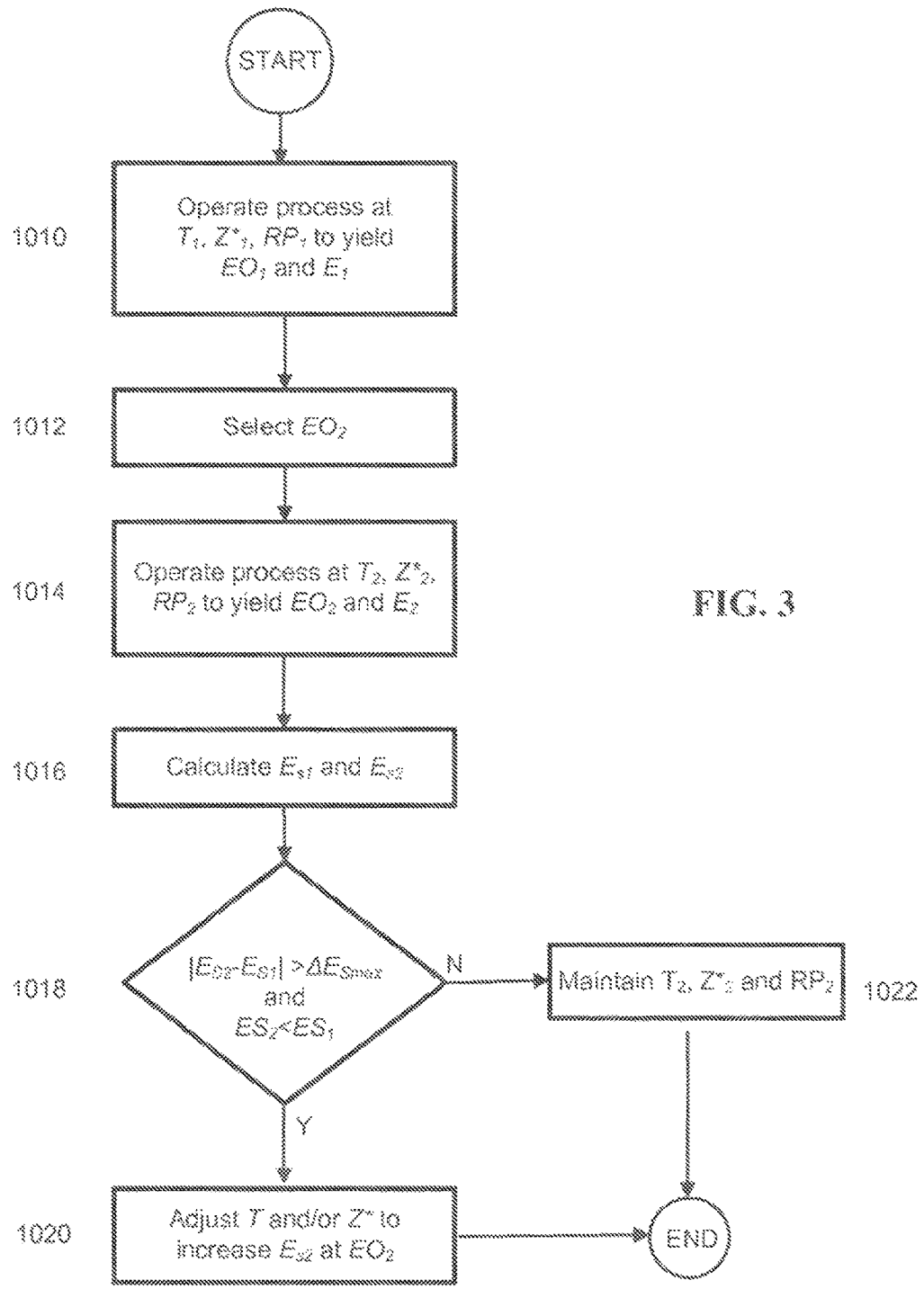
FIG. 3 is a flowchart depicting a method of operating a process for producing ethylene oxide using scaled selectivity values to determine if an adjustment to the reaction temperature and/or overall catalyst chloriding effectiveness is required to move the process toward an optimum condition.

Referring to FIG. 3, a flow chart depicting a method of making ethylene oxide using scaled selectivity values is provided. In accordance with the method, a feed gas comprising ethylene, oxygen, and at least one organic chloride moderator is reacted over a silver, high-efficiency catalyst comprising rhenium. In step 1010 the process is operated at a first reaction temperature value $T_1$, a first value of the overall catalyst chloriding effectiveness $Z^*_1$, and a set of first values $RP_1$ for a set of reference operating conditions comprising a plurality of reaction parameters to yield a first value $EO_1$ of a target ethylene oxide production parameter. The set of reference operating conditions preferably comprises at least one ethylene oxide production parameter (which may be the target ethylene oxide production parameter and/or another ethylene oxide production parameter), a carbon dioxide concentration, an oxygen concentration, a gas hourly space velocity, and a reactor pressure. Each of the individual parameter values may correspond to a reactor inlet condition, a reactor outlet condition, or an average along the catalyst bed. Operation at $T_1$, $Z^*_1$, and $RP_1$ yields an actual selectivity value of $E_1$ at the first value $EO_1$ of the target ethylene oxide production parameter.

In step 1012 a new value of the target ethylene oxide production parameter $EO_2$ is selected. In order to achieve the new value $EO_2$, in step 1014 the process is operated at a second reaction temperature value $T_2$, a second overall catalyst chloriding effectiveness value $Z^*_2$, and a set of second values $RP_2$ for the set of reference operating conditions. As a result, the actual selectivity changes to $E_2$, and the process is operated at the new desired value $EO_2$ of the selected target ethylene oxide production parameter. The words "first" and "second" do not necessarily indicate that particular values have changed. Instead, they are used to distinguish the state of the process at different points in time. However, the values of at least one of the (i) reaction temperature, (ii) overall catalyst chloriding effectiveness, and (iii) at least one operating condition from the set of reference operating conditions will change in step 1014 relative to step 1010 to change the value of the target ethylene oxide production parameter to its new desired value $EO_2$.

In step 1016 the scaled selectivity values $E_{S2}$ and $E_{S1}$ are calculated using any of the techniques described previously. At least one reference operating condition is selected to carry out the calculation. The at least one reference operating condition will have a corresponding reference value, and corresponding values in the first set of values from step 1010 and in the second set of values from step 1014. The at least one reference operating condition preferably comprises at least one ethylene oxide production parameter and may further comprise at least one of an oxygen concentration, an ethylene concentration, a reactor pressure, and a gas hourly space velocity. The values of these conditions may be reactor inlet, reactor outlet, or catalyst bed average values based on one or more measurements along the catalyst bed. If each reference value of the at least one reference operating condition is the same as the corresponding value of the at least one reference operating condition in the set $RP_1$, the calculation of $E_{S1}$ will be unnecessary or trivial as it will be the same as $E_1$. A similar situation applies to the relationship between $E_2$ and $ES_2$.

In step 1018 the absolute value of the difference between the scaled selectivity values $E_{S2}$ and $E_{S1}$ is calculated and compared to the maximum difference value $\Delta E_{Smax}$, and the values of $E_{S2}$ and $E_{S1}$ are compared to see if $E_{S2}$ is less than $E_{S1}$ (this can be collapsed into a single statement wherein $E_{S2}-E_{S1}$ is compared to $\Delta E_{Smax}$ without taking an absolute value of $E_{S2}-E_{S1}$). If step 1018 returns a value of TRUE (or YES), the process has moved farther away from optimum operation. Thus, in step 1020 reaction temperature and/or overall chloriding effectiveness are adjusted to increase the value of $E_{S2}$ while maintaining the desired value of the target ethylene oxide production parameter at $EO_2$. Preferably, $E_{S2}$ is increased to at least the value of $E_{S1}$. In certain preferred examples, at least one controller is provided and includes a program stored in the controller memory which comprises a set of executable steps which, when executed by a computer processor, automatically calculate scaled selectivity values as the reaction temperature and/or overall catalyst chloriding effectiveness are adjusted. If step 1018 returns a value of FALSE (or NO), in step 1022 the values of the reaction temperature, overall catalyst chloriding effectiveness, and the set of reference operating conditions (reaction parameters) are maintained at their values $T_2$, $Z^*_2$, and $RP_2$ from step 1014.

The adjusting step 1020 preferably comprises an optimization step. The optimization preferably comprises varying combinations of the reaction temperature and overall catalyst chloriding effectiveness while maintaining the desired value $EO_2$ of the target ethylene oxide production parameter. Suitable optimization methods are known to those in the art. In accordance with one method, a variety of different reaction temperatures are selected and held constant while varying the overall catalyst chloriding effectiveness value and maintaining the concentrations of ethylene and oxygen, the reactor pressure, and the gas hourly space velocity constant. The method will yield a unique combination of the reaction temperature and overall catalyst chloriding effectiveness value that provides both a maximum selectivity and the desired value $EO_2$ of the target ethylene oxide production parameter. It should be noted that the actual temperature that is manipulated, while still being directly or indirectly indicative of reaction temperature, may not be the same as the temperature used in calculating scaled selectivity values in step 1016. For example, a reactor outlet gas temperature may be used as a reference operating condition in $RP_1$ and $RP_2$ to calculate the scaled selectivity values $ES_1$ and $ES_2$, while the temperature manipulated in step 1020 may be a reactor coolant inlet temperature.

In accordance with certain examples, the difference between the scaled reaction temperatures at two different sets of operating conditions may be used to determine the direction(s) in which to adjust reaction temperature and/or overall catalyst chloriding effectiveness when the absolute value of the difference between the scaled selectivities at the two different sets of operating conditions exceeds the selected value, $\Delta E_{SMAX}$. The scaled reaction temperatures may be compared as follows:

$$|T_{S2}-T_{S1}|>\Delta T_{Smax} \quad (7)$$

wherein, $T_{S1}$ is a scaled reaction temperature (° C.) calculated based on the value in a first set of values of at least one of the reference operating conditions in a set of reference operating conditions and a reference value of the at least one of the reference operating conditions in the set of reference operating conditions, $T_{S2}$ is a scaled reaction temperature (° C.) calculated based on the value in a second set of values of the at least one of the reference operating conditions in the set of reference operating conditions and the reference value of the at least one of the reference operating conditions in the set of reference operating conditions, and $\Delta T_{Smax}$ is a selected maximum (° C.) of the absolute value of the difference of scaled reaction temperatures.

In general, if the inequality in equation (7) is satisfied, it means the catalyst has become relatively more or less chlorided than before, i.e. the chlorination state has changed. Whether the catalyst is actually underchlorided or overchlorided in an absolute sense will also depend on whether the scaled selectivity has increased or decreased as a result of changing the process from the first set of operating conditions to the second set of operating conditions. If equation (7) is not satisfied, adjustments to the values of reaction temperature and/or overall catalyst chloriding effectiveness may still be desirable if equation (6) is satisfied. However, in that case, the scaled reaction temperatures will not provide an indication of the specific directions in which the reaction temperature and/or overall catalyst chloriding effectiveness should be adjusted to move toward optimal operation. Preferred values of $\Delta T_{Smax}$ will depend on the accuracy and reliability of the measurements and model used to determine scaled reaction temperature values. The value of $\Delta T_{Smax}$ is preferably set no lower than the reliability of reference operating condition measurements and the scaled reaction temperature model will allow. In certain examples, the value of $\Delta T_{Smax}$ is from about 0.5° C. to about 1.5° C.

If the inequalities in equations (6) and (7) are both satisfied, the values of $E_{S2}$, $E_{S1}$, $T_{S2}$ and $T_{S1}$ may be used to determine the appropriate directions in which to adjust the reaction temperature and/or the overall catalyst chloriding effectiveness (while maintaining the desired value of a target ethylene oxide production parameter) as shown in Table 1 below. In Table 1 it is assumed that $E_{S1}$ and $T_{S1}$ correspond to an initial set of values of reference operating conditions which is subsequently changed to a second set of values of the reference operating conditions which correspond to $E_{S2}$ and $T_{S2}$, and that the indicated adjustments are carried out while maintaining a second selected value of a target ethylene oxide production parameter to which $E_{S2}$ and $T_{S2}$ correspond:

TABLE 1

| | $E_{S2} > E_{S1}$ | $E_{S2} < E_{S1}$ |
|---|---|---|
| $T_{S2} > T_{S1}$ | Catalyst was likely overchlorided at the first set of operating conditions and is less chlorided at the second set of operating conditions but still may be overchlorided. Increase reaction temperature and/or decrease overall catalyst chloriding effectiveness | Catalyst is underchlorided Decrease reaction temperature and/or increase overall catalyst chloriding effectiveness. |
| $T_{S2} < T_{S1}$ | Catalyst was likely underchlorided at the first set of operating conditions and is more chlorided at the second set of operating conditions but still may be underchlorided. Decrease reaction temperature and/or overall increase catalyst chloriding effectiveness. | Catalyst is overchlorided Increase reaction temperature and/or decrease overall catalyst chloriding effectiveness. |

Figure 4:
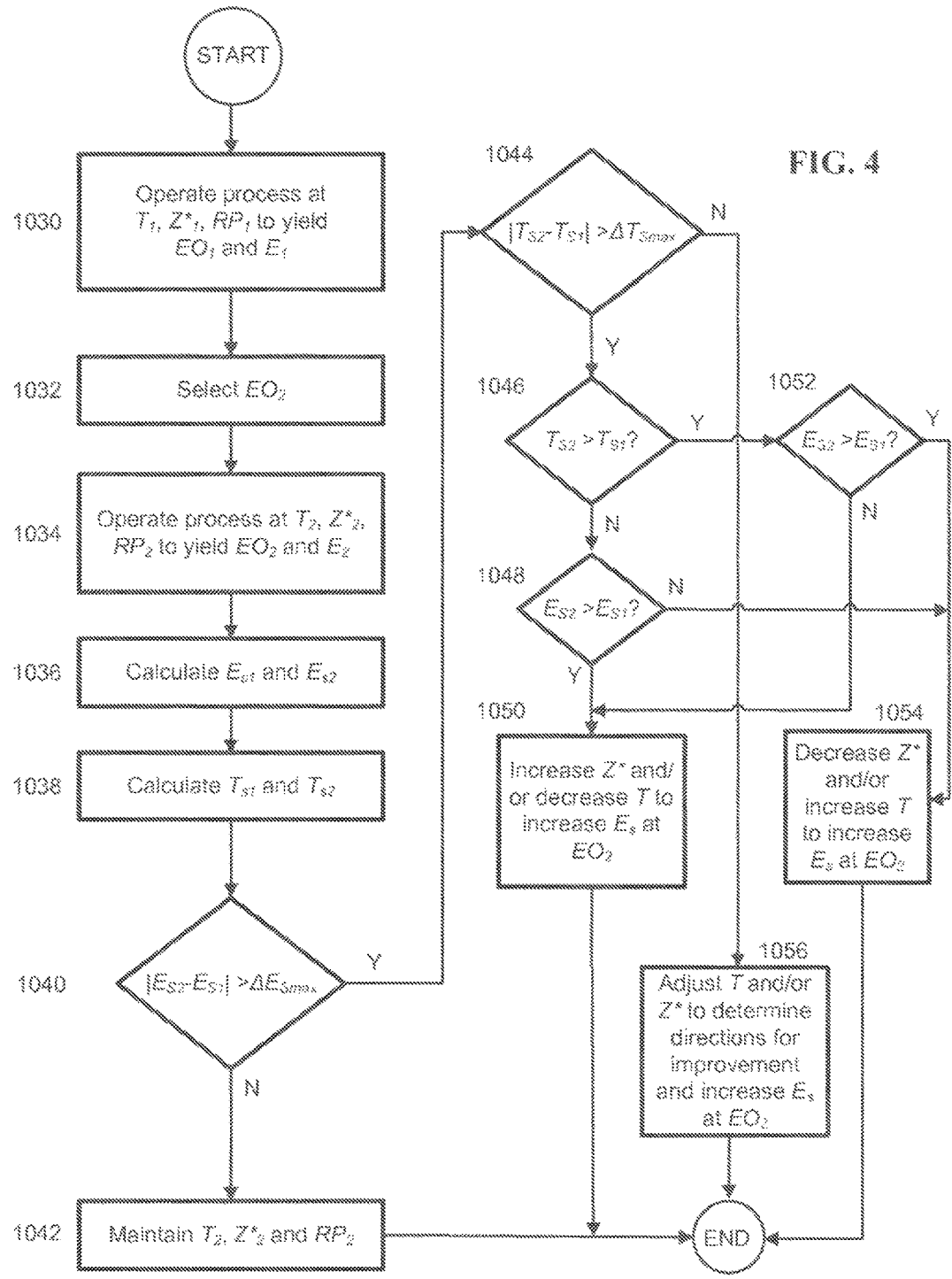
FIG. 4 is a flowchart depicting a method of operating a process for producing ethylene oxide using scaled selectivity values and scaled temperature values to determine if an adjustment to the reaction temperature and/or overall catalyst chloriding effectiveness is required to move the process toward an optimum condition as well as the directions in which to adjust the reaction temperature and overall catalyst chloriding effectiveness.

Referring to FIG. 4, a flow chart depicting another method of making ethylene oxide using scaled selectivity values is provided. In accordance with the method, a feed gas comprising ethylene, oxygen, and at least one organic chloride moderator is reacted over a silver, high-efficiency catalyst comprising rhenium. In step 1030 the process is operated at a first reaction temperature value $T_1$, a first value of the overall catalyst chloriding effectiveness $Z^*_1$, and a set of first values $RP_1$ for a set of reference operating conditions comprising a plurality of reaction parameters to yield a first value $EO_1$ of a selected target ethylene oxide production parameter. The set of reference operating conditions preferably comprises at least one ethylene oxide production parameter (which may be the target ethylene oxide production parameter and/or another ethylene oxide production parameter), a carbon dioxide concentration, an oxygen concentration, a gas hourly space velocity, and a reactor pressure. Each of the individual reaction parameter values may correspond to a reactor inlet condition, a reactor outlet condition, or an average value along the catalyst bed. Operation at $T_1$, $Z^*_1$, and $RP_1$ yields an actual selectivity value of $E_1$ at the first value $EO_1$ of the target ethylene oxide production parameter.

In step 1032 a new value of the target ethylene oxide production parameter $EO_2$ is selected. In order to achieve the new value $EO_2$, in step 1034 the process is operated at a second reaction temperature value $T_2$, a second overall catalyst chloriding effectiveness value $Z^*_2$, and a set of second values $RP_2$ of the set of reference operating conditions. As a result, the actual selectivity changes to $E_2$, and the process is operated at the new selected target ethylene oxide production parameter value $EO_2$. The words "first" and "second" do not necessarily indicate that particular values have changed. Instead, they are used to distinguish the state of the process at different points in time. However, the values of at least one of (i) the reaction temperature, (ii) the overall catalyst chloriding effectiveness, and (iii) at least one operating condition from the set of reference operating conditions will change in step 1034 relative to step 1030 to change the value of the ethylene oxide production parameter.

In step 1036 the scaled selectivity values $E_{S2}$ and $E_{S1}$ are calculated using any of the techniques described previously. At least one reference operating condition is selected to carry out the calculations. The at least one reference operating condition will have a corresponding reference value and corresponding values in the first set of values $RP_1$ from step 1030 and the second set of values $RP_2$ from step 1034. The at least one reference operating condition preferably comprises at least one ethylene oxide production parameter (which may be the target parameter corresponding to the value $EO_1$) and may further comprise at least one of an oxygen concentration, an ethylene concentration, a reactor pressure, and a gas hourly space velocity. The values of these conditions may be reactor inlet, reactor outlet, or catalyst bed average values based on one or more measurements along the catalyst bed. If each reference value of the at least one reference operating condition is the same as the corresponding value of the at least one reference operating condition in the set $RP_1$, the calculation of $E_{S1}$ will be unnecessary as it will be the same as $E_1$. A similar situation may apply to the relationship between $E_2$ and $E_{S2}$.

In step 1038 the scaled reaction temperature values $T_{S2}$ and $T_{S1}$ are calculated using any of the techniques described previously. At least one reference operating condition is used to carry out the calculations. The at least one reference operating condition will have a corresponding reference value, and a corresponding value in the first set of values $RP_1$ from step 1030 and the second set of values $RP_2$ from step 1034. The at least one reference operating condition preferably comprises at least one ethylene oxide production parameter (which may be the target parameter corresponding to the value $EO_1$) and may further comprise at least one of an oxygen concentration, an ethylene concentration, a reactor pressure, and a gas hourly space velocity. The values of these conditions may be reactor inlet, reactor outlet, or catalyst bed average values based on one or more measurements along the catalyst bed. If each reference value of the at least one reference operating condition is the same as the corresponding value of the at least one reference operating condition in the set $RP_1$, the calculation of $T_{S1}$ will be unnecessary as it will be the same as $T_1$. The same holds for $T_{S2}$. The (first) at least one reference operating condition used to calculate scaled selectivities in step 1036 may be the same as or different from the (second) at least one reference operating condition used to calculate scaled reaction temperature values in step 1038.

In step 1040 the absolute value of the difference between the scaled selectivity values $E_{S2}$ and $E_{S1}$ is calculated and compared to the maximum difference value $\Delta E_{Smax}$. If step 1040 returns a value of FALSE (or NO), the process has not moved any farther away from optimum as a result of the adjustments made in step 1034 and the process ends. Otherwise step 1044 is carried out.

In step 1044 the absolute value of the difference of the scaled reaction temperature values $T_{S1}$ and $T_{S2}$ is calculated and compared to the selected maximum difference $\Delta T_{Smax}$. If step 1044 returns a value of FALSE (or NO), the scaled reaction temperatures are not indicative of the direction(s) in which to change the reaction temperature and/or the overall catalyst chloriding effectiveness value in order to move the process closer to optimum operation. Accordingly, in step 1056 the reaction temperature and/or the overall catalyst chloriding effectiveness are adjusted, for example, using known trial-and-error methods such as those described above, to determine the directions for improvement and to increase the scaled selectivity value while maintaining the desired target ethylene oxide production parameter value $EO_2$.

If step 1044 returns a value of TRUE (or YES), then the scaled reaction temperatures $T_{S1}$ and $T_{S2}$ may be used in conjunction with the scaled selectivity values $E_{S1}$ and $E_{S2}$ to determine the appropriate directions in which to change the reaction temperature and/or the overall catalyst chloride effectiveness to improve selectivity at the current target value of an ethylene oxide production parameter $EO_2$. In step 1046 the scaled second reaction temperature value $T_{S2}$ is compared to the scaled first reaction temperature $T_{S1}$. If the scaled second reaction temperature value $T_{S2}$ is greater than the scaled first reaction temperature value $T_{S1}$, control transfers to step 1052 and the scaled selectivities $E_{S2}$ and $E_{S1}$ are compared. If the scaled second selectivity value $E_{S2}$ is greater than the scaled first selectivity value $E_{S1}$, even though the process has relatively improved, i.e. is "more optimal", as a result of the adjustments made in step 1034, the catalyst may still be overchlorided relative to optimum conditions and the initial conditions in step 1030 were likely sub-optimal. Thus, in step 1054 the reaction temperature is increased and/or the overall catalyst chloriding effectiveness value is decreased to determine whether this further increases the scaled selectivity while also maintaining the current target value $EO_2$ of an ethylene oxide production parameter. If the scaled selectivity does not increase, the previous values of reaction temperature and overall catalyst chloriding effectiveness ($T_2$ and $Z^*_2$) are preferably restored.

If the scaled second selectivity value $E_{S2}$ is less than the scaled first selectivity value $E_{S1}$ in step 1052, the catalyst is underchlorided. Thus, in step 1050 the overall catalyst chloriding effectiveness is increased and/or the reaction temperature is decreased in a manner that increases the scaled selectivity (preferably to $E_{S1}$) while maintaining the current target value $EO_2$ of an ethylene oxide production parameter.

In step 1046 if the scaled second reaction temperature $T_{S2}$ is less than the scaled first reaction temperature $T_{S1}$, control transfers to step 1048 and the scaled selectivity values $E_{S1}$ and $E_{S2}$ are compared. If the scaled second selectivity value $E_{S2}$ is greater than the scaled first selectivity value $E_{S1}$, even though the process has relatively improved, i.e. is "more optimal", as a result of the adjustments made in step 1034, the catalyst may still be underchlorided relative to optimum conditions and the initial conditions in step 1030 were likely sub-optimal. Thus, control transfers to step 1050, and the overall catalyst chloriding effectiveness is increased and/or the reaction temperature is decreased to determine whether this further increases the scaled selectivity while maintaining the current target value $EO_2$ of an ethylene oxide production parameter. If the scaled selectivity does not increase, the previous values of reaction temperature and overall catalyst chloriding effectiveness ($T_2$ and $Z^*_2$) are preferably restored.

In step 1048 if the scaled second selectivity value $E_{S2}$ is less than the scaled first selectivity value $E_{S1}$, the catalyst is overchlorided. Thus, control transfers to step 1054, and the reaction temperature is increased and/or the overall catalyst chloriding effectiveness value is decreased in a manner that increases the scaled selectivity (preferably to $E_{S1}$) while also maintaining the current target value $EO_2$ of an ethylene oxide production parameter.

Steps 1050, 1054, and 1056 are preferably optimization steps. Suitable optimization steps are known to those skilled in the art. The optimization preferably comprises varying combinations of the reaction temperature and overall catalyst chloriding effectiveness while maintaining the desired value $EO_2$ of a target ethylene oxide production parameter value. Suitable optimization methods are known to those of skill in the art. In accordance with one method, a variety of different reaction temperatures are selected and held constant while varying the overall catalyst chloriding effectiveness value and maintaining the concentrations of ethylene and oxygen, the reactor pressure, and the gas hourly space velocity. The method will yield a unique combination of the reaction temperature and overall catalyst chloriding effectiveness value that provides both a maximum selectivity (or at least returns the process to the scaled first selectivity value $E_{S1}$) and the desired target value $EO_2$ of the ethylene oxide production parameter. If steps 1050 or 1054 are carried out, the optimizations are performed by moving reaction temperature and/or overall catalyst chloriding effectiveness in the directions indicated in FIG. 4, which expedites and simplifies the optimization process.

Thus, the combined use of scaled selectivity and scaled reaction temperature values provides the unexpected benefit that the process can be more readily re-optimized when necessary because the appropriate directions for adjusting the reaction temperature and/or overall catalyst chloriding effectiveness can, in some instances, be discerned.

A projection of the expected selectivity, temperature, and/or production over the life of the catalyst may be done at the anticipated operating conditions for the plant throughout the life of the catalyst. The projection may include assumptions about changes in certain operating conditions over catalyst life caused by, e.g., expected constraints known to those of skill in the art such as, maximum reactor temperature limits, $CO_2$ removal efficiency, and reactant availability. Alternatively, a projection may be done at fixed reaction conditions, for example, at the reference values of the reference operating conditions as used for a scaled parameter calculation. Monitoring the scaled parameters as a function of time or other measure of catalyst age and comparing them with the projection at the set of reference conditions provides additional insight into the performance of the catalyst.

In principle, if the scaled selectivity is lower than the projected selectivity as the catalyst ages, optimization of chlorides should be conducted to increase the selectivity to optimum. Trends in the slopes of the scaled parameters over time compared to the slopes of the projections are useful to determine whether the scaled selectivity is falling faster than expected, whether or not the catalyst optimization is improving performance, or whether the catalyst needs more or less chlorination. For example, if the scaled selectivity is lower than expected and the scaled temperature is rising faster than the projection, the catalyst may be relatively underchlorided and need more chlorides to increase selectivity. On the other hand, if the scaled temperature is not changing as fast as projected, then the catalyst may be relatively overchlorided and need less chlorides.

The scaled parameter method is exemplified by the following non-limiting examples.

EXAMPLES

Experiment 1 illustrates how process or laboratory data may be used to determine the parametric effect of delta EO (as a reference operating condition $x_i$) on selectivity and temperature. Table 2 below shows three sets of operating conditions A, B, and C where all conditions are held constant except for delta EO. For each set of operating conditions, Table 3 reports the actual reaction temperature and selectivity obtained at the efficiency-maximizing value of Z* given the target values for delta EO (i.e. from a starting combination of temperature and Z* yielding a desired value of delta EO, T and Z* are varied in opposite directions to maintain delta EO until efficiency is maximized).

TABLE 2

|  | A | B | C |
| --- | --- | --- | --- |
| Inlet CO$_2$% | 1.6 | 1.6 | 1.6 |
| Inlet O$_2$% | 8.2 | 8.2 | 8.2 |
| Inlet C$_2$H$_4$% | 35 | 35 | 35 |
| Inlet pressure (psia) | 310 | 310 | 310 |
| Bed volume based GHSV | 5400 | 5400 | 5400 |
| ΔEO % | 2.20 | 1.80 | 2.40 |

TABLE 3

|  | A | B | C |
| --- | --- | --- | --- |
| Temperature (° C.) at optimum Z* | 240.3 | 235.3 | 242.8 |
| Selectivity (%) | 87.3 | 88.5 | 86.7 |

Start with a generalized linear form for scaled temperature.

$$T_r = T + \sum_{i=1}^{n} \frac{dT}{dx_i}(x_{ir} - x_i) \tag{5}$$

Since only one operating condition varies in the experiment, i=1, and the equation can be reduced to:

$$T_r = T + \frac{dT}{dx}(x_r - x) \tag{8}$$

where x is delta EO (mole-%). The equation can be rearranged to calculate dT/dx:

$$\frac{dT}{dx} = (T_r - T)/(x_r - x) \tag{9}$$

Using the values in Table 2 corresponding to the set of operating conditions A as the reference values, dT/dx can be calculated from the values in Table 2 and 3 for the set of operating conditions B as shown below.

$T_r$=240.3, T=235.3, $T_r$ −T=5.0° C.
$x_r$=2.20, x=1.80, $x_r$−x=0.40 mole-%
dT/dx=5.0/0.40=12.5° C./mole-%

Alternatively, over the broader range of delta EO corresponding to sets of operation conditions B and C, dT/dx is again calculated as:

dT/dx=(235.3−242.8)/(1.80−2.40)=−7.5/−0.60=12.5° C./mole-%

The scaled temperature equation for the case where all conditions are constant except for delta EO then becomes:

$$T_r = T + 12.5(x_r - x) \tag{10}$$

The effect of delta EO on selectivity is determined in a similar manner. Start with a generalized linear form for scaled selectivity.

$$E_r = E + \sum_{i=1}^{n} \frac{dE}{dx_i}(x_{ir} - x_i) \tag{4}$$

Since only one operating condition varies in the experiment, i=1, and the equation can be reduced to:

$$E_r = E + \frac{dE}{dx}(x_r - x) \tag{11}$$

where x is delta EO (mole-%). The equation can be rearranged to calculate dE/dx.

$$\frac{dE}{dx} = = (E_r - E)/(x_r - x) \tag{12}$$

Using the values for the set of operating conditions A as the reference values, dT/dx can be calculated from the values for the set of operating conditions B as shown below.

$E_r$=87.3, E=88.5, $E_r$ −E=−1.2%
$x_r$=2.20, x=1.80, $x_r$−x=0.40 mole-%
dE/dx=−1.2/0.40=−3.0%/mole-%

Alternatively, using the sets of operating conditions A and C, dE/dx can be calculated as:

dE/dx=(87.3−86.7)/(2.20−2.40)=0.6/−0.20=−3.0%/mole-%

The scaled selectivity equation for the case where all conditions are constant except for delta EO then becomes $$E_r = E - 3.0(x_r - x) \tag{13}$$

Analogous experiments can be carried out to determine the coefficients of other variables in the scaling model. The experiments can be performed by varying only one reference operating condition at a time (in each case varying temperature and Z* as needed to optimize efficiency at the desired value of an ethylene oxide production parameter), or preferably with a designed set of experiments coupled with statistical fitting of the data.

Experiment 2 illustrates how process or laboratory data may be used to determine the parametric effect of inlet CO$_2$ concentration (mole-%) on selectivity and temperature. Table 4 below shows three sets of operating conditions A, B, and C where all conditions are constant except for inlet CO$_2$. Table 5 shows the actual temperature and selectivity at the efficiency-maximizing value of Z* for each set of operating conditions.

TABLE 4

|  | A | B | C |
|---|---|---|---|
| Inlet CO$_2$% | 1.6 | 0.8 | 1.2 |
| Inlet O$_2$% | 8.2 | 8.2 | 8.2 |
| Inlet C$_2$H$_4$% | 35 | 35 | 35 |
| Inlet pressure (psia) | 310 | 310 | 310 |
| Bed volume based GHSV | 5400 | 5400 | 5400 |
| ΔEO % | 2.20 | 2.20 | 2.20 |

TABLE 5

|  | A | B | C |
|---|---|---|---|
| Temperature (° C.) at optimum Z* | 240.3 | 238.3 | 239.3 |
| Selectivity (%) | 87.3 | 87.5 | 87.4 |

Using equations 9 and 12 with the operating variable x equal to inlet CO$_2$ concentration (mole-%), dT/dx and dE/dx are determined to be 2.5° C./mole-% CO$_2$ and −0.25%/mole-% CO$_2$, respectively. Combining the effect of delta EO from Experiment 1 and the effect of inlet CO$_2$ concentration from Experiment 2 gives the following pair of equations (14, 15) which can be used when both CO$_2$ (mole-%) and delta EO change at the same time.

$$T_r = T + 12.5(x_{1r} - x_1) + 2.5(x_{2r} - x_2) \quad (14)$$

$$E_r = E - 3.0(x_{1r} - x_1) - 0.25(x_{2r} - x_2) \quad (15)$$

where $x_1$ is delta EO, $x_2$ is inlet CO$_2$ (mole-%), and the subscript r, refers to the corresponding reference values.

Example 1

In this example, an EO plant is operating at a first set of operating conditions D (Table 6) where the catalyst is known to be optimized. The operating conditions are changed to a second set of operating conditions E (Table 6). Neither set of values in the sets of operating conditions D and E completely correspond to the set of reference values for the set of reference operating conditions (Table 7). The actual selectivity, temperature, and Z* obtained at the sets of operating conditions D and E are shown in Table 8. The value of $\Delta E_{Smax}$ is taken to be 0.1%.

TABLE 6

| Two sets of operating conditions | | |
|---|---|---|
|  | D | E |
| Inlet CO$_2$% | 1.6 | 1.0 |
| Inlet O$_2$% | 8.2 | 8.2 |
| Inlet C$_2$H$_4$% | 35 | 35 |
| Inlet pressure (psia) | 310 | 310 |
| Bed volume based GHSV | 5400 | 5400 |
| ΔEO % | 1.80 | 2.30 |

TABLE 7

| Reference conditions | |
|---|---|
|  | Reference |
| Inlet CO$_2$% | 1.6 |
| Inlet O$_2$% | 8.2 |
| Inlet C$_2$H$_4$% | 35 |
| Inlet pressure (psia) | 310 |
| Bed volume based GHSV | 5400 |
| ΔEO % | 2.20 |

TABLE 8

Actual selectivity, actual temperature, and Z* for the two sets of operating conditions D and E for Example 1

|  | D | E |
|---|---|---|
| Temperature (° C.) | 235.3 | 240.1 |
| Selectivity (%) | 88.5 | 87.1 |
| Z* | 3 | 4.4 |

Scaled selectivity and temperature for conditions D and E are calculated with equations 14 and 15 and are listed in Table 9.

TABLE 9

Scaled temperature and selectivity for Example 1

|  | D | E |
|---|---|---|
| Scaled Temperature (° C.) | 240.3 | 240.35 |
| Scaled Selectivity (%) | 87.3 | 87.25 |

Since the absolute value of the difference between the scaled selectivities for the sets of operating conditions D and E is less than $\Delta E_{Smax}$, and the catalyst is known to be optimized at the set of operating conditions D, then the catalyst is considered to be still optimized at the set of operating conditions E and no further adjustment of temperature and/or Z* is needed.

Example 2

In this example, the EO plant is again operating at a first set of operating conditions D (Table 6) where the catalyst is known to be optimized. As before, the operating conditions are changed to a second set of operating conditions E (Table 6). However, for Example 2, a different combination of temperature and Z* is used to obtain the desired delta EO of 2.30 mole-% at the set of reaction conditions E, and the resulting actual selectivity is also different from that obtained in Example 1, as shown in Table 10. For Example 2, the values of $\Delta E_{Smax}$ and $\Delta T_{Smax}$ are taken to be 0.1% and 0.5° C., respectively.

TABLE 10

Actual selectivity, actual temperature, and Z* for the two sets of operating conditions D and E for Example 2

|  | D | E |
|---|---|---|
| Temperature (° C.) | 235.3 | 242.1 |
| Selectivity (%) | 88.5 | 86.3 |
| Z* | 3 | 3.9 |

Using the set of reference values for the set of reference conditions from Table 7, the scaled selectivity and temperature for the sets of operating conditions D and E are calculated for the results in Table 10 with equations 14 and 15 (Table 11).

TABLE 11

Scaled temperature and selectivity for Example 2

|  | D | E |
|---|---|---|
| Scaled Temperature (° C.) | 240.3 | 242.35 |
| Scaled Selectivity (%) | 87.3 | 86.45 |

Since the absolute value of the difference between the scaled selectivities is greater than $\Delta E_{Smax}$ and the scaled selectivity is lower for the set of operating conditions E than for D, where the catalyst is already known to be optimized, then the catalyst is not optimized at the set of operating conditions E. Since the absolute value of the difference between the scaled temperatures is greater than $\Delta T_{Smax}$ and the scaled temperature is higher for the set of operating conditions E than for D, the catalyst is thus determined to be underchlorided, and temperature is subsequently decreased while Z* is increased to improve efficiency while maintaining a delta EO of 2.30 mole-%.

Example 3

In this example, the plant is again operating at a first set of operating conditions D (Table 6) where the catalyst is known to be optimized. The operating conditions are changed to a second set of operating conditions E (Table 6). However, for Example 3, yet another combination of temperature and Z* is used to obtain the desired delta EO of 2.30 mole-% at the set of reaction conditions E, and the resulting actual selectivity is also different from those obtained in Examples 1 and 2, as shown in Table 12. For Example 3, the values of $\Delta E_{Smax}$ and $\Delta T_{Smax}$ are taken to be 0.1% and 0.5° C., respectively.

TABLE 12

Actual selectivity, actual temperature, and Z* for the two sets of operating conditions D and E for Example 3

|  | D | E |
|---|---|---|
| Temperature (° C.) | 235.3 | 238.1 |
| Selectivity (%) | 88.5 | 86.0 |
| Z* | 3 | 5 |

Using the set of reference values for the set of reference conditions from Table 7, the scaled selectivity and temperature for the sets of operating conditions D and E are calculated for the results in Table 12 with equations 14 and 15 (Table 13).

TABLE 13

Scaled temperature and selectivity for Example 3

|  | D | E |
|---|---|---|
| Scaled Temperature (° C.) | 240.3 | 238.35 |
| Scaled Selectivity (%) | 87.3 | 86.15 |

Since the absolute value of the difference between the scaled selectivities is greater than $\Delta E_{Smax}$ and the scaled selectivity is lower for the set of operating conditions E than for D, where the catalyst is already known to be optimized, then the catalyst is not optimized at the set of operating conditions E. Since the absolute value of the difference between the scaled temperatures is greater than $\Delta T_{Smax}$ and the scaled temperature is lower for the set of operating conditions E than for D, the catalyst is thus determined to be overchlorided, and temperature is subsequently increased while Z* is decreased to improve efficiency while maintaining a delta EO of 2.30 mole-%.

What is claimed is:

1. A method of operating a process for producing ethylene oxide by reacting a feed gas comprising ethylene, oxygen, and at least one organic chloride over a high selectivity, silver-based catalyst comprising rhenium, the method comprising the steps of:
   operating the process at a first value of a reaction temperature, a first value of an overall catalyst chloriding effectiveness, and a first set of values for a set of reference operating conditions, the set of reference operating conditions comprising a plurality of reference reaction parameters, to yield a first value of a target ethylene oxide production parameter and a first actual selectivity value;
   operating the process at a second value of the reaction temperature, a second value of the overall catalyst chloriding effectiveness, and a second set of values for the set of reference operating conditions, to yield a second value of the target ethylene oxide production parameter and a second actual selectivity value;
   calculating a scaled second selectivity value from the second actual selectivity, a value in the second set of values of at least one of the reference operating conditions in the set of reference operating conditions, and a reference value of the at least one of the reference operating conditions in the set of reference operating conditions;
   determining that an adjustment is required to at least one of the reaction temperature and the overall catalyst chloriding effectiveness based on the scaled second selectivity value and the first actual selectivity value, and subsequently
   adjusting at least one of the reaction temperature to a third reaction temperature value and the overall catalyst chloriding effectiveness to a third overall catalyst chloriding effectiveness value, such that the scaled selectivity increases, wherein the reference operating conditions in the set of reference operating conditions are selected from the group consisting of reactor inlet pressure, reactor outlet pressure, gas hourly space velocity, composition of a reactor feed stream, concentrations of components in a reactor feed stream, composition of a reactor product stream, average compositions of components taken along a bed of the high-selectivity, silver-based catalyst, average pressure along a bed of the high-selectivity, silver-based catalyst, concentrations of components in a reactor product stream, and any ethylene oxide production parameters selected from the group consisting of ethylene oxide concentration, ethylene oxide yield, ethylene oxide production rate, ethylene oxide production rate/catalyst volume, ethylene conversion, and oxygen conversion.

2. The method of claim 1, wherein the step of calculating a scaled second selectivity value from the second actual selectivity, the value in the second set of values of at least one of the reference operating conditions in the set of reference operating conditions, and a reference value of the at least one of the reference operating conditions in the set of reference operating conditions comprises calculating the scaled second selectivity value using a selectivity scaling relationship selected from the group consisting of a linear relationship and a non-linear relationship.

3. The method of claim 1, wherein the step of determining that an adjustment is required to at least one of the reaction temperature and the overall catalyst chloriding effectiveness comprises comparing an absolute value of a difference between the scaled second selectivity value and the first actual selectivity value to a pre-determined value.

4. The method of claim 1, further comprising the step of calculating a scaled first selectivity value from the first actual selectivity value, a value in the first set of values of the at least one of the reference operating conditions in the set of reference operating conditions, and the reference value of the at least one of the reference operating conditions in the set of reference operating conditions, wherein the step of determining that an adjustment is required to at least one of the reaction temperature and the overall catalyst chloriding effectiveness is based on the scaled second selectivity value and the scaled first selectivity value.

5. The method of claim 1, wherein each reference operating condition in the set of reference operating conditions has a reference value, and each reference value for each reference operating condition in the set of reference operating conditions differs from the corresponding value in the first set of values for the set of reference operating conditions and the corresponding value in the second set of values for the set of reference operating conditions.

6. The method of claim 1, wherein the set of reference operating conditions includes an ethylene oxide production parameter selected from the group consisting of ethylene oxide concentration, ethylene oxide yield, ethylene oxide production rate, ethylene oxide production rate/catalyst volume, ethylene conversion, and oxygen conversion.

7. The method of claim 6, wherein the set of reference operating conditions further includes at least one selected from the group consisting of an oxygen concentration, an ethylene concentration, a carbon dioxide concentration, a reactor pressure, and a gas hourly space velocity.

8. The method of claim 1, wherein the step of adjusting at least one of the reaction temperature to a third reaction temperature value and the overall catalyst chloriding effectiveness to a third overall catalyst chloriding effectiveness value comprises adjusting the at least one of the reaction temperature to a third reaction temperature value and the overall catalyst chloriding effectiveness to a third overall catalyst chloriding effectiveness value until the second scaled selectivity value is observed at the second value of the target ethylene oxide production parameter.

9. The method of claim 4, wherein the at least one of the reference operating conditions in the set of reference operating conditions is a first at least one of the reference operating conditions in the set of reference operating conditions, the method further comprising the steps of:
calculating a scaled second reaction temperature value from the second value of the reaction temperature, a value in the second set of values of a second at least one of the reference operating conditions in the set of reference operating conditions, and a reference value of the second at least one of the reference operating conditions in the set of reference operating conditions, wherein the step of adjusting at least one of the reaction temperature to a third reaction temperature value and the overall catalyst chloriding effectiveness to a third overall catalyst chloriding effectiveness value is further based on the scaled second reaction temperature and the first value of the reaction temperature.

10. The method of claim 9, wherein the step of calculating a scaled second reaction temperature value from the second value of the reaction temperature, the value in the second set of values of the second at least one of the reference operating conditions in the set of reference operating conditions, and a reference value of the second at least one of the reference operating conditions in the set of reference operating conditions comprises calculating the scaled second reaction temperature value using a reaction temperature scaling relationship selected from the group consisting of a linear relationship and a non-linear relationship.

11. The method of claim 9, further comprising the step of calculating a scaled first reaction temperature value from the first value of the reaction temperature, a value in the first set of values of the second at least one of the reference operating conditions in the set of reference operating conditions, and a reference value of the second at least one of the reference operating conditions in the set of reference operating conditions, wherein the step of adjusting at least one of the reaction temperature to a third reaction temperature value and the overall catalyst chloriding effectiveness to a third overall catalyst chloriding effectiveness value is further based on the scaled second reaction temperature and the scaled first reaction temperature value.

12. The method of claim 11, wherein the step of operating the process at a first value of the reaction temperature, a first value of the overall catalyst chloriding effectiveness, and a first set of values for the set of reference operating conditions occurs before the step of operating the process at a second value of the reaction temperature, a second value of the overall catalyst chloriding effectiveness, and a second set of values for the set of reference operating conditions, the scaled second selectivity is less than the scaled first selectivity by more than a first predetermined value, the scaled second reaction temperature value is lower than the scaled first reaction temperature value by more than a second predetermined value, and the step of adjusting at least one of the reaction temperature to a third reaction temperature value and the overall catalyst chloriding effectiveness to a third overall catalyst chloriding effectiveness value comprises at least one of increasing the reaction temperature to the third reaction temperature value and decreasing the overall catalyst chloriding effectiveness to the third overall catalyst chloriding effectiveness value.

13. A method of operating a process for producing ethylene oxide by reacting a feed gas comprising ethylene, oxygen, and at least one organic chloride over a high selectivity, silver-based catalyst comprising rhenium, the method comprising the steps of:
operating the process at a first value of a reaction temperature, a first value of an overall catalyst chloriding effectiveness, and a first set of values for a set of reference operating conditions, the set of reference operating conditions comprising a plurality of reference reaction parameters, to yield a first value of a target ethylene oxide production parameter and a first actual selectivity value;
subsequently operating the process at a second value of the reaction temperature, a second value of the overall catalyst chloriding effectiveness, and a second set of values for the set of reference operating conditions, to yield a second value of the target ethylene oxide production parameter and a second actual selectivity value;
calculating a scaled first selectivity value from the first actual selectivity value, a value in the first set of values of a first at least one of the reference operating conditions in the set of reference operating conditions, and a reference value of the first at least one of the reference operating conditions in the set of reference operating conditions;

calculating a scaled second selectivity value from the second actual selectivity value, a value in the second set of values of the first at least one of the reference operating conditions in the set of reference operating conditions, and the reference value of the first at least one of the reference operating conditions in the set of reference operating conditions;

calculating a scaled first reaction temperature value from the first value of the reaction temperature, a value in the first set of values of a second at least one of the reference operating conditions in the set of reference operating conditions, and a reference value of the second at least one of the reference operating conditions in the set of reference operating conditions;

calculating a scaled second reaction temperature value from the second value of the reaction temperature, a value in the second set of values of the second at least one of the reference operating conditions in the set of reference operating conditions, and the reference value of the second at least one of the reference operating conditions in the set of reference operating conditions;

determining that an adjustment is required to at least one of the reaction temperature and the overall catalyst chloriding effectiveness by comparing the scaled first selectivity to the scaled second selectivity; and subsequently adjusting at least one of the reaction temperature to a third reaction temperature value and the overall catalyst chloriding effectiveness to a third overall catalyst chloriding effectiveness value, such that the scaled selectivity increases, wherein the step of subsequently adjusting is based on the first scaled selectivity value, the second scaled selectivity value, the first scaled reaction temperature, and the second scaled reaction temperature, wherein the reference operating conditions in the set of reference operating conditions are selected from the group consisting of reactor inlet pressure, reactor outlet pressure, gas hourly space velocity, composition of a reactor feed stream, concentrations of components in a reactor feed stream, composition of a reactor product stream, average compositions of components taken along a bed of the high-selectivity, silver-based catalyst, average pressure along a bed of the high-selectivity, silver-based catalyst, concentrations of components in a reactor product stream, and any ethylene oxide production parameters selected from the group consisting of ethylene oxide concentration, ethylene oxide yield, ethylene oxide production rate, ethylene oxide production rate/catalyst volume, ethylene conversion, and oxygen conversion.

14. The method of claim 13, wherein the steps of calculating a scaled first selectivity value and a scaled second selectivity value comprise calculating the scaled first selectivity value and the scaled second selectivity value using a selectivity scaling relationship selected from the group consisting of a linear relationship and a non-linear relationship.

15. The method of claim 13, wherein the steps of calculating a scaled first reaction temperature value and a scaled second reaction temperature value comprise calculating the scaled first reaction temperature value and the scaled second reaction temperature value using a reaction temperature scaling relationship selected from the group consisting of a linear relationship and a non-linear relationship.

* * * * *